(12) United States Patent
Nakajima et al.

(10) Patent No.: US 12,017,033 B2
(45) Date of Patent: Jun. 25, 2024

(54) FLUID CONTROL DEVICE FOR ENDOSCOPE AND ENDOSCOPE

(71) Applicant: OLYMPUS CORPORATION, Tokyo (JP)

(72) Inventors: Sho Nakajima, Hachioji (JP); Masahiko Murayama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 872 days.

(21) Appl. No.: 17/064,742

(22) Filed: Oct. 7, 2020

(65) Prior Publication Data
US 2021/0016075 A1    Jan. 21, 2021

Related U.S. Application Data

(63) Continuation of application No. PCT/JP2019/004869, filed on Feb. 12, 2019.

(30) Foreign Application Priority Data

Apr. 11, 2018   (JP) .................................. 2018-076032

(51) Int. Cl.
*A61M 39/10* (2006.01)
*A61B 1/00* (2006.01)
(Continued)

(52) U.S. Cl.
CPC ....... *A61M 39/105* (2013.01); *A61B 1/00128* (2013.01); *A61B 1/015* (2013.01);
(Continued)

(58) Field of Classification Search
CPC ................ A61M 39/105; A61M 39/22; A61M 2039/1044; A61M 2205/44;
(Continued)

(56) References Cited

U.S. PATENT DOCUMENTS 5,042,467 A  *  8/1991  Foley ................ A61M 15/0086
                                                128/200.14
5,347,992 A  *  9/1994  Pearlman ................. A61B 1/12
                                                  600/131
(Continued)

FOREIGN PATENT DOCUMENTS

EP      3009077 A1    4/2016
JP    S59-151929 A    8/1984
(Continued)

OTHER PUBLICATIONS

International Search Report dated Apr. 9, 2019 issued in PCT/JP2019/004869.

*Primary Examiner* — John P Leubecker
(74) *Attorney, Agent, or Firm* — Scully, Scott, Murphy & Presser, P.C.

(57) ABSTRACT

A gas feeding/suction valve includes: a cylinder including a conduit opening communicable with a fluid conduit of an endoscope; two coupling members provided at different positions from the conduit opening of the cylinder and connected to respective fluid sources; and an operation member provided inside the cylinder and including a shaft slidably disposed in a space forming respective fluid paths through which openings of the two coupling members and the conduit opening communicate with each other, and the cylinder includes a sounding body provided near at least one of two ventilation ports, through which the fluid paths communicate with an outside of the cylinder, and configured to generate a warning sound when a fluid flows in a direction opposite to a direction in which a fluid generated from the fluid source is supposed to flow.

15 Claims, 12 Drawing Sheets

(51) Int. Cl.
*A61B 1/015* (2006.01)
*A61M 39/22* (2006.01)

(52) U.S. Cl.
CPC ..... *A61M 39/22* (2013.01); *A61M 2039/1044* (2013.01); *A61M 2205/44* (2013.01)

(58) Field of Classification Search
CPC . A61B 1/00128; A61B 1/015; A61B 1/00066; A61B 1/00068; A61B 1/012
See application file for complete search history.

(56) References Cited

U.S. PATENT DOCUMENTS

| | | | |
|---|---|---|---|
| 6,346,075 B1 * | 2/2002 | Arai | A61B 1/00068 600/159 |
| 2006/0030751 A1 | 2/2006 | Uesugi et al. | |
| 2015/0305599 A1 * | 10/2015 | Murayama | A61B 1/00119 600/159 |
| 2016/0106934 A1 | 4/2016 | Hiraga et al. | |
| 2017/0189589 A1 * | 7/2017 | Zachar | A61M 1/741 |

FOREIGN PATENT DOCUMENTS

| | | |
|---|---|---|
| JP | 2009-018053 A | 1/2009 |
| JP | WO 2010/116562 A | 10/2010 |
| WO | WO 2015/019695 A1 | 2/2015 |

* cited by examiner

FLUID CONTROL DEVICE FOR ENDOSCOPE AND ENDOSCOPE

CROSS REFERENCE TO RELATED APPLICATION

This application is a continuation application of PCT/JP2019/004869 filed on Feb. 12, 2019 and claims benefit of Japanese Application No. 2018-076032 filed in Japan on Apr. 11, 2018, the entire contents of which are incorporated herein by this reference.

BACKGROUND OF THE INVENTION

1. Field of the Invention

The present invention relates to a fluid control device for endoscope that is detachably attached to a mounting portion provided on an operation portion of an endoscope, and an endoscope including the fluid control device for endoscope.

2. Description of the Related Art

A medical endoscope generally includes an insertion portion that is inserted into a body cavity and an operation portion provided on a proximal end side of the insertion portion. Some endoscopes include an insertion portion provided with a fluid conduit (channel) for gas feeding, water feeding, or suction.

In the endoscope provided with such a channel, a fluid control device is provided in the mounting portion provided on the operation portion, and can control gas feeding, water feeding, and suction with a finger of the hand holding the operation portion.

In recent years, an endoscope has been used in which a gas/water feeding fluid control device equipped with a gas feeding pipe sleeve and a suction pipe sleeve is provided in one mounting portion provided on the operation portion of the endoscope and gas feeding and suction can be performed through the conduit provided in the insertion portion.

International Publication No. 2010/116562 discloses a fluid control device for endoscope in which a cylinder detachably attached to an endoscope body does not come off accidentally even when a load is applied from a fluid tube.

According to such a fluid control device for endoscope, a gas feeding leak hole of the fluid control device for endoscope is closed with, for example, an index finger of the hand holding the operation portion, and thus compressed air flows from a channel opening into a body cavity. On the other hand, when an operation button of the fluid control device for endoscope is pushed, a liquid in the body cavity can be sucked from the channel opening through an insertion channel and a conduit.

In such a fluid control device for endoscope, a valve body portion configured to close a suction path is provided in order to eliminate a problem that a gas feeding tube is erroneously connected to a suction pipe sleeve and excessive gas is fed into the body cavity, and gas is avoided from being fed through the suction path.

SUMMARY OF THE INVENTION

A fluid control device for endoscope according to an aspect of the present invention includes: a cylinder that is attachable to an operation portion of an endoscope and includes a conduit opening communicable with a fluid conduit provided inside an insertion portion of the endoscope; two coupling members provided at different positions from the conduit opening of the cylinder and connected to respective fluid sources configured to execute predetermined functions; and an operation member provided inside the cylinder and including a shaft slidably disposed in a space forming respective fluid paths through which openings of the two coupling members and the conduit opening communicate with each other, wherein the cylinder includes a sounding body provided near at least one of two ventilation ports, through which the fluid paths communicate with an outside of the cylinder and configured to generate a warning sound when a fluid flows in a direction opposite to a direction in which a fluid generated from the fluid source is supposed to flow.

An endoscope according to another aspect of the present invention includes: an insertion portion including a fluid conduit therein; an operation portion provided continuously to the insertion portion; and a fluid control device for endoscope, the fluid control device for endoscope including: a cylinder that is attachable to the operation portion and includes a conduit opening communicable with a fluid conduit provided inside the insertion portion; two coupling members provided at different positions from the conduit opening of the cylinder and connected to respective fluid sources configured to execute predetermined functions; and an operation member provided inside the cylinder and including a shaft slidably disposed in a space forming respective fluid paths through which openings of the two coupling members and the conduit opening communicate with each other, the cylinder including a sounding body provided near at least one of two ventilation ports, through which the fluid paths communicate with an outside of the cylinder and configured to generate a warning sound when a fluid flows in a direction opposite to a direction in which a fluid generated from the fluid source is supposed to flow.

DETAILED DESCRIPTION OF THE PREFERRED EMBODIMENT

Figure 1:
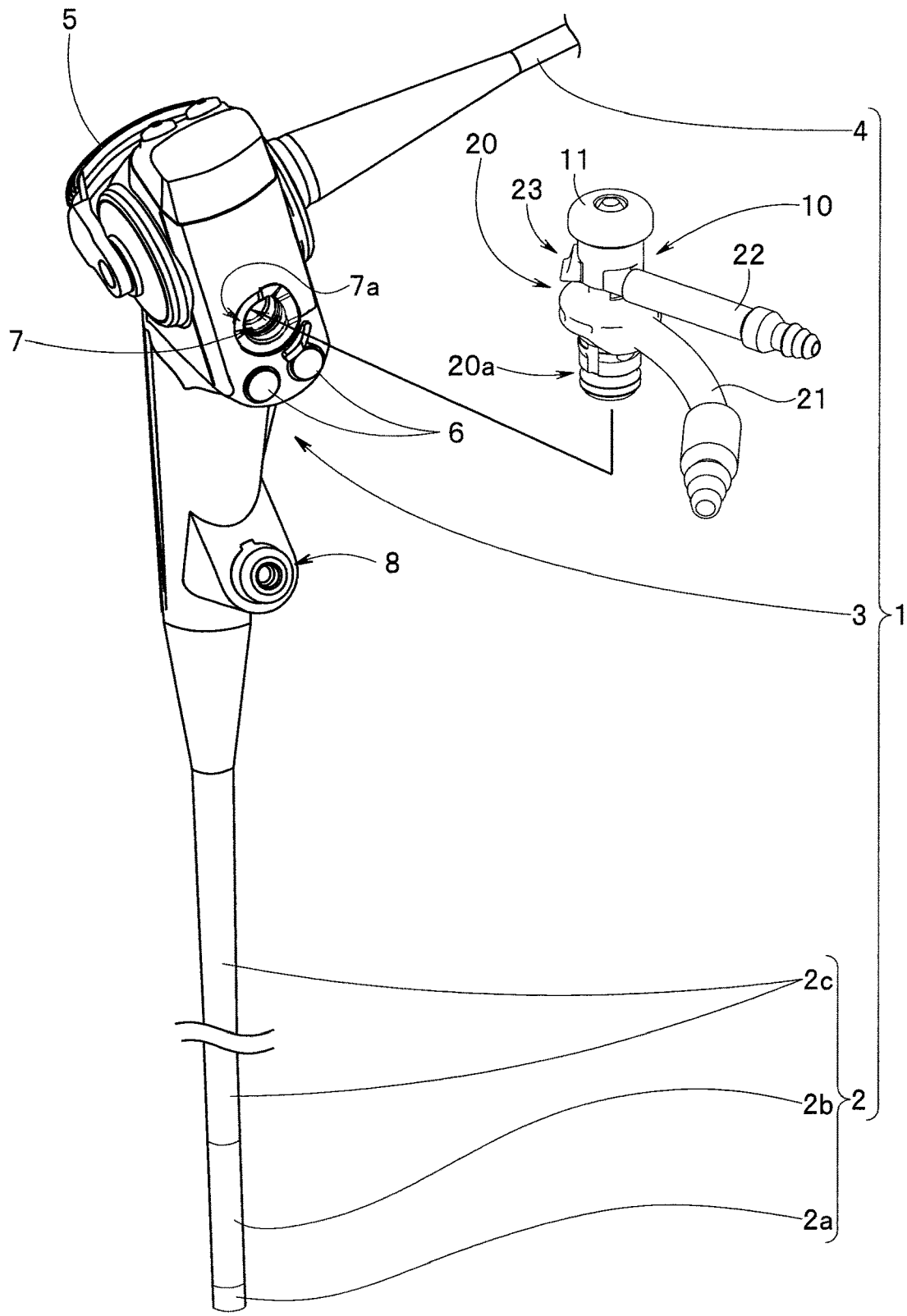
FIG. 1 is a view illustrating an endoscope and a fluid control device for endoscope.

An embodiment of the present invention will be described below with reference to the drawings.

Note that, in each of the drawings used in the following description, scales are varied for each component to show the respective components in recognizable sizes in the drawings. In other words, the present invention is not limited only to numbers of the components, shapes of the components, ratios of sizes of the components, and relative positional relations among the respective components shown in the drawings.

As shown in FIG. 1, an endoscope 1 includes an insertion portion 2, an operation portion 3, and a universal cable 4. Reference numeral 10 denotes a fluid control device for endoscope (hereinafter, referred to as a gas feeding/suction valve).

The insertion portion 2 is an elongated long member that is inserted into a subject which is a site to be observed. The insertion portion 2 includes a distal end portion 2a, a bending portion 2b, and a flexible tube portion 2c which are provided in this order from a distal end side. The bending portion 2b is configured to be bendable in two directions of up and down, for example. The flexible tube portion 2c is a long tubular member having flexibility.

The bending portion 2b may be configured to be bendable in four directions of up, down, left, and right. In addition, the insertion portion 2 may be configured such that a rigid tube portion is continuously provided on a proximal end side of the bending portion 2b instead of the flexible tube portion 2c.

The operation portion 3 is provided with a bending operation portion 5, various switches 6, a mounting portion 7, and a treatment instrument insertion port 8, etc. The bending operation portion 5 is operated to bend the bending portion 2b. The various switches 6 are, for example, a release switch, a freeze switch, or an observation mode changeover switch configured to switch between normal observation and fluorescence observation.

An engaging member 20a of the gas feeding/suction valve 10 is detachably attached to the mounting portion 7. A treatment instrument is inserted through the treatment instrument insertion port 8. The treatment instrument passes through a channel tube for treatment instrument insertion (not shown) and is guided to the outside from an opening for treatment instrument channel (not shown) of the distal end portion 2a.

The universal cable 4 extends from a side of the operation portion 3. An endoscope connector (not shown) is provided at an end portion of the universal cable 4. The endoscope connector is detachably attached to a camera control unit including a light source device which is an external device.

Figure 4A:
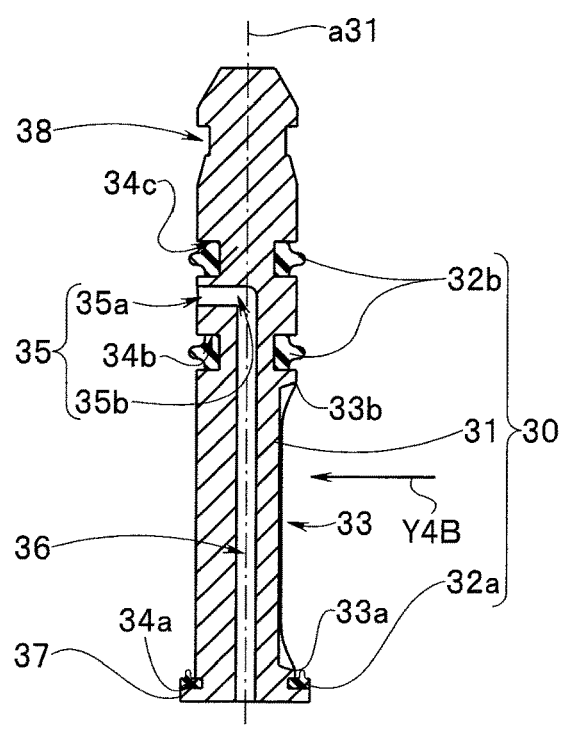
FIG. 4A is a cross-section view taken along the line Y3C-Y3C in FIG. 3B and illustrates a shaft of a piston portion.

The gas feeding/suction valve 10 includes a cylindrical cylinder 20 having an internal space and an operation member (see reference numeral 30 in FIG. 4A). Reference numeral 21 denotes a suction pipe sleeve, reference numeral 22 denotes a gas feeding pipe sleeve, and reference numeral 23 denotes a leak dimple having an inclined surface, which also serves as a sounding body, and provided to protrude toward an outer peripheral surface of the cylinder 20. Reference numeral 11 denotes an operation button. The operation button 11 is attached to one end side of a shaft (see reference numeral 31 in FIG. 4A) forming the operation member 30. An outer side of the operation button 11 is an operation surface, which is touched by a finger during a pushing operation.

The cylinder 20 will be described with reference to FIGS. 2A to 3C.

Figure 2A:
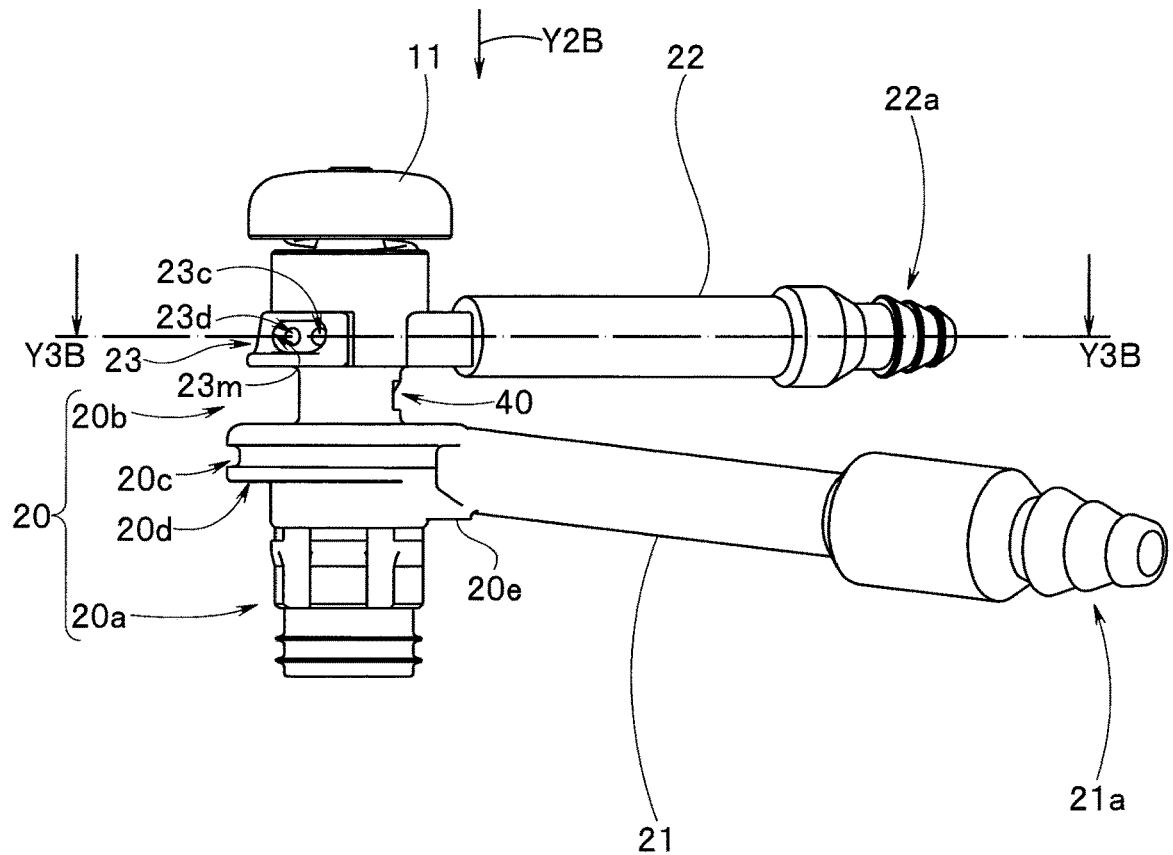
FIG. 2A is a view illustrating the fluid control device for endoscope.

As shown in FIG. 2A, the cylinder 20 includes an engaging member 20a and a cylinder body 20b. The engaging member 20a is a portion attached to the inside of the mounting portion 7. The cylinder body 20b is a portion protruding outward from the exterior of the operation portion 3.

Reference numeral 20c denotes an abutting flange. The abutting flange 20c includes a cylinder abutting surface 20d that abuts on an end surface (see reference numeral 7b in FIG. 6A) of the mounting portion 7. Reference numeral 20e denotes a positioning member. The positioning member 20e is provided in an engaging portion (see reference numeral 7a in FIG. 1) of the mounting portion 7 to define an orientation of the gas feeding/suction valve 10 with respect to the mounting portion 7.

Figure 2B:
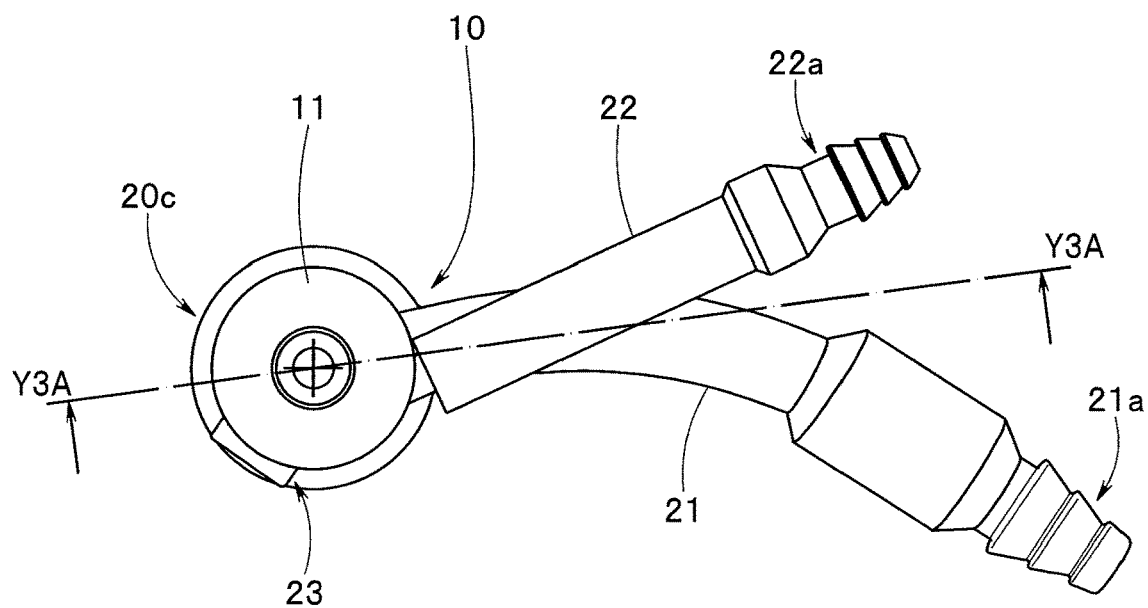
FIG. 2B is a view of the fluid control device for endoscope as viewed from a direction of an arrow Y2B in FIG. 2A.

As shown in FIGS. 2A and 2B, the tubular suction pipe sleeve 21 and gas feeding pipe sleeve 22 and the leak projection 23 protrude from the outer peripheral surface of the cylinder body 20b. In FIG. 2A, reference numeral 40 denotes a sounding body (a first sounding body) to be described below, and is provided in a suction hole (see reference numeral 24h in FIG. 3A).

An end portion of the suction pipe sleeve 21 serves as a coupling member 21a of a suction tube. A suction tube (see reference numeral 51 in FIG. 6A) extending from a suction source is connected to the coupling member 21a of the suction tube, the suction source being one of fluid sources and having a suction function. An end portion of the gas feeding pipe sleeve 22 serves as a coupling member 22a of a gas feeding tube. A gas feeding tube (see reference numeral 52 in FIG. 6A) extending from a gas feeding source is connected to the coupling member 22a of the gas feeding tube, the gas feeding source being one of fluid sources and having a gas feeding function.

A configuration of the cylinder 20 and a relation between the suction pipe sleeve 21 and a shaft holding hole 25 will be described with reference to FIG. 3A.

Figure 3A:
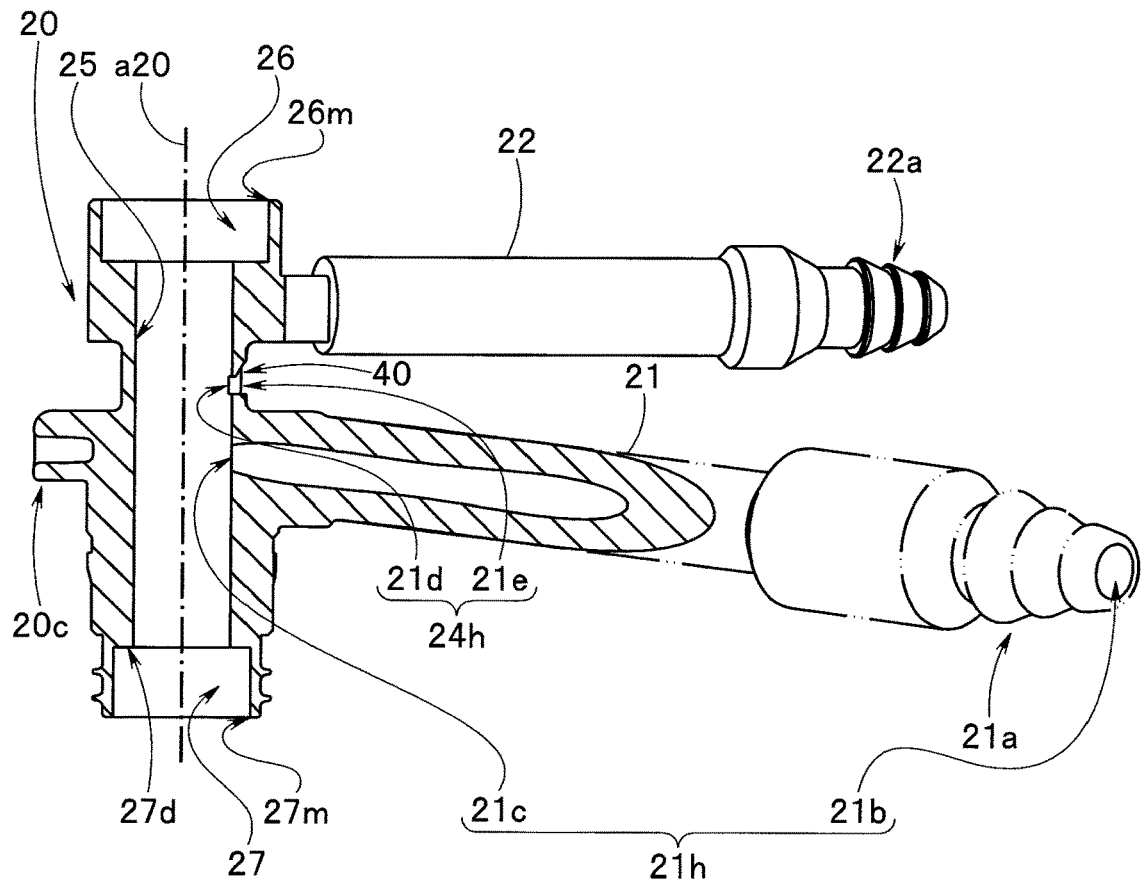
FIG. 3A is a cross-section view taken along a line Y3A-Y3A in FIG. 2B and mainly illustrates a shaft holding hole and a suction pipe sleeve through-hole of a cylinder.

As shown in FIG. 3A, the cylinder 20 includes the shaft holding hole 25 that is a through-hole along a cylinder longitudinal axis a20. The shaft holding hole 25 includes an outer side opening 26*m* which is one side opening of the cylinder longitudinal axis a20 and a conduit opening 27*m* which is the other side opening. The coupling members 21*a* and 22*a* are provided at positions different from the conduit opening 27*m*.

The outer side opening 26*m* is an opening of a dimple for biasing member 26. For example, a compression coil spring (see reference numeral 12 in FIG. 5A) is provided in the dimple for biasing member 26. The compression coil spring 12 has a predetermined elastic force, and is set to a predetermined height. Reference numeral 26*d* denotes a spring installation surface.

The conduit opening 27*m* is an opening of an insertion portion conduit-side dimple 27, and communicates with a fluid conduit (see reference numeral 2*ch* in FIG. 6A) provided in the insertion portion 2. Reference numeral 27*d* denotes a flange abutting surface.

Reference numeral 21*h* denotes a suction pipe sleeve through-hole. The suction pipe sleeve through-hole 21*h* includes a suction port 21*b* that is one opening at an end of the coupling member 21*a* of the suction tube and communicates with the outside. The other opening of the suction pipe sleeve through-hole 21*h* is a first side hole 21*c*, and is provided at a predetermined position of the shaft holding hole 25.

Then, the suction port 21*b* and the conduit opening 27*m* communicate with each other through the suction pipe sleeve through-hole 21*h*, the shaft holding hole 25, and the insertion portion conduit-side dimple 27.

Reference numeral 24*h* is a suction hole, and includes a second side hole 21*d* communicating with the shaft holding hole 25 and an intake port 21*e* that is a ventilation port communicating with the outside. A sounding body 40 is provided near the intake port 21*e*.

The second side hole 21*d* is located at a predetermined position of the shaft holding hole 25, and is distant upwards from a first side hole 21*c* by a predetermined distance. The suction port 21*b* and the intake port 21*e* communicate with each other through the suction hole 24*h* and the shaft holding hole 25.

Figure 3B:
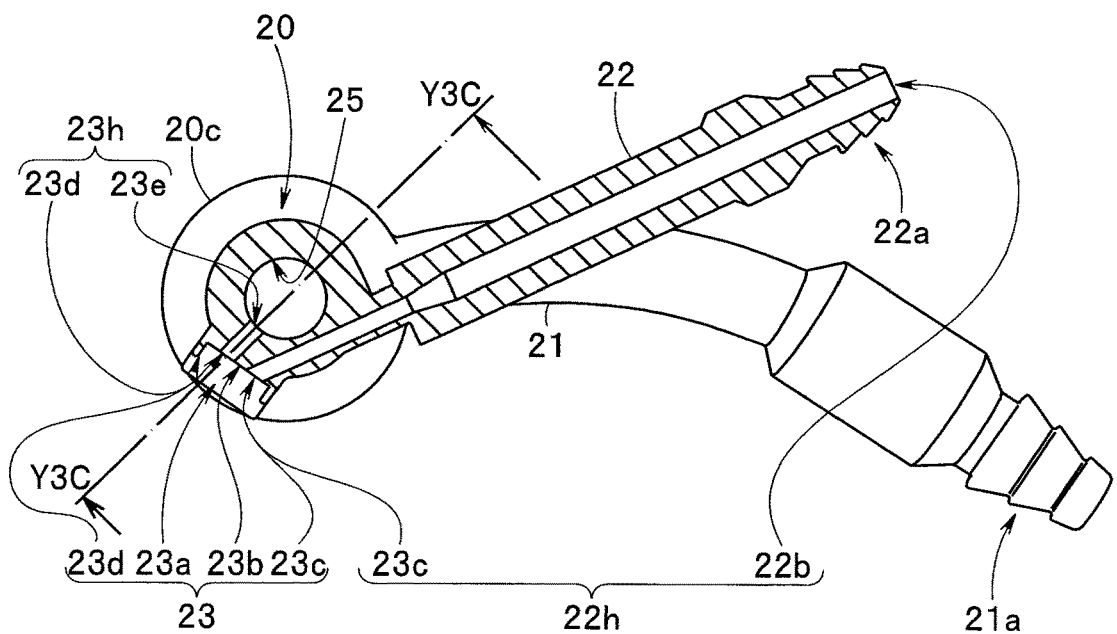
FIG. 3B is a cross-section view taken along a line Y3B-Y3B in FIG. 2A and illustrates a shaft holding hole, a gas feeding pipe sleeve through-hole, and a leak dimple of the cylinder.
Figure 3C:
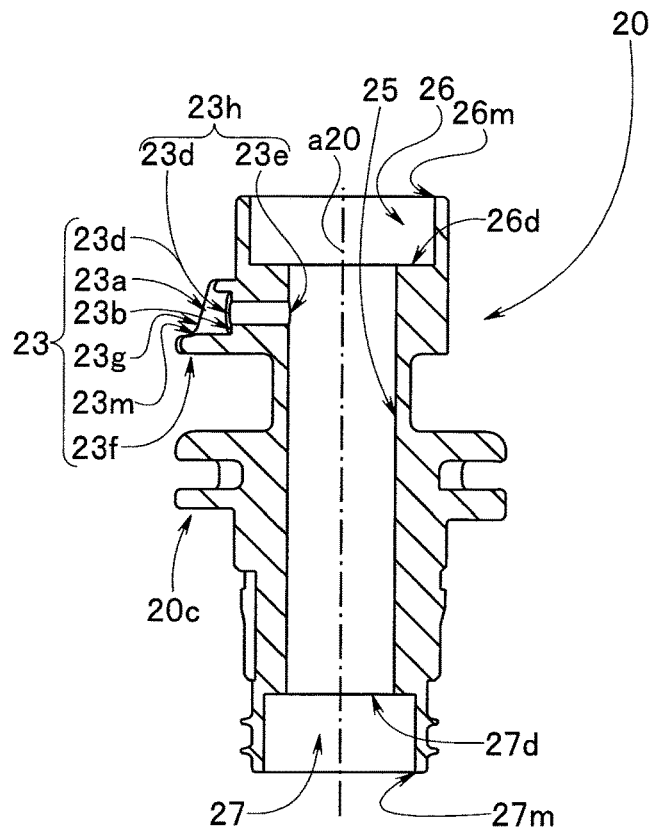
FIG. 3C is a cross-section view taken along a line Y3C-Y3C in FIG. 3B and mainly illustrates a shaft holding hole and a leak dimple of the cylinder.

With reference to FIGS. 3B and 3C, a description will be given with respect to a configuration of the leak projection 23 and a relation between the leak projection 23, the gas feeding pipe sleeve 22, and the shaft holding hole 25.

First, the configuration of the leak projection 23 will be described.

As shown in FIGS. 3B and 3C, a dimple 23*a* is provided in the leak projection 23. Reference numeral 23*m* denotes a dimple opening that is a ventilation port opened toward the outside. Reference numeral 23*b* denotes a dimple bottom-surface. The dimple bottom-surface 23*b* is provided with a first dimple opening 23*c* as a jet port and a second dimple opening 23 d as an inlet port. The first dimple opening 23*c* and the second dimple opening 23*d* are provided adjacent to the dimple bottom-surface 23*b*.

The relation between the gas feeding pipe sleeve 22 and the leak projection 23 will be described below.

As shown in FIG. 3B, the gas feeding pipe sleeve 22 includes a gas feeding pipe sleeve through-hole 22*h*. The gas feeding pipe sleeve through-hole 22*h* includes a gas feeding port 22*b* that is one opening at the end of the coupling member 22*a* of the gas feeding tube and communicates with the outside. The other opening of the gas feeding pipe sleeve through-hole 22*h* is the first dimple opening 23*c* communicating with the dimple 23*a*. A second sounding body (see reference numeral 40A in FIG. 7B) is provided near the first dimple opening 23*c* serving as a jet port.

The relation between the leak projection 23 and the shaft holding hole 25 will be described below.

Reference numeral 23*h* shown in FIGS. 3B and 3C denotes a gas feeding through-hole. The gas feeding through-hole 23*h* is an inlet port in which the second dimple opening 23*d* provided in the dimple 23*a* of the leak projection 23 is one opening. The other opening of the gas feeding through-hole 23*h* is a gas feeding communication port 23*e* communicating with the shaft holding hole 25.

In a state where the dimple opening 23*m* is closed, the gas feeding port 22*b* and the conduit opening 27*m* communicate with each other through the gas feeding pipe sleeve through-hole 22*h*, the dimple 23*a*, the gas feeding through-hole 23*h*, the shaft holding hole 25, and the insertion portion conduit-side dimple 27.

The gas feeding port 22*b* and the dimple opening 23*m* are ventilation passages for gas feeding that communicate with the outside through the gas feeding pipe sleeve through-hole 22*h* and the dimple 23*a*. In addition, reference numeral 23*f* denotes an eaves portion, which protrudes from an end surface 23*g* of the dimple opening 23*m*.

The operation member 30 will be described with reference to FIGS. 4A and 4B.

Figure 4B:
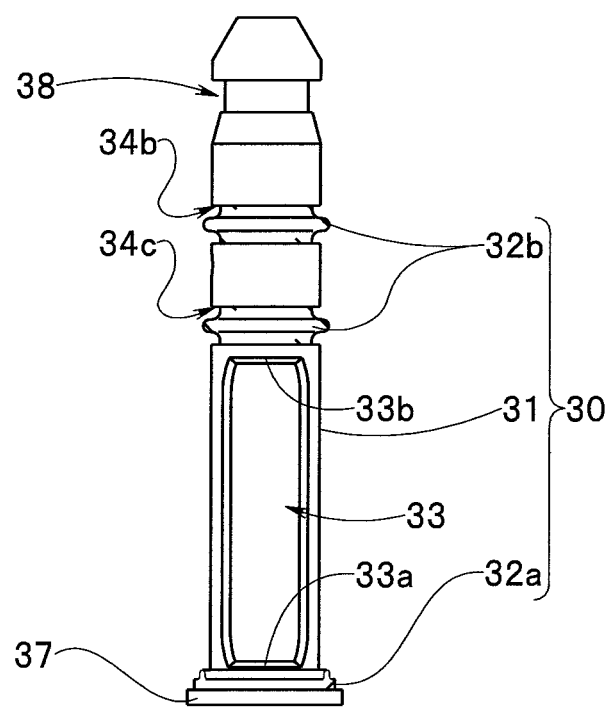
FIG. 4B is a view of the shaft as viewed in a direction of an arrow Y4B in FIG. 4A.

As shown in FIGS. 4A and 4B, the operation member 30 is a piston portion and includes a shaft 31 provided with seal members 32*a* and 32*b*. Each of the seal members 32*a* and 32*b* has a predetermined elastic force.

In addition, the shaft 31 includes a suction communication dimple 33 that functions as a communication path at the time of forming a fluid path for suction, a dimple communication hole 35 that functions as a communication path at the time of forming a fluid path for gas feeding, and a gas feeding hole 36.

The suction communication dimple 33 is a cavity formed with a predetermined depth on the outer peripheral surface of the shaft 31. One end side 33*a* of the suction communication dimple 33 is provided at a predetermined position near an outer flange portion 37, and the other end side 33*b* thereof is provided at a predetermined position near a second circumferential groove 34*b* to be described below.

The shaft 31 is disposed inside the shaft holding hole 25, which is an internal space of the cylinder 20, and is slidable. An outer diameter of the shaft 31 is smaller than an inner diameter of the shaft holding hole 25. Accordingly, a gap (see reference numeral 13 in FIG. 5A) is formed between the outer peripheral surface of the shaft 31 and an inner peripheral surface of the shaft holding hole 25.

The shaft 31 is formed with three circumferential grooves (a first circumferential groove 34*a* in which the first seal member 32*a* is provided, and a second circumferential groove 34*b* and a third circumferential groove 34*c* in which the second seal members 32*b* are provided, respectively).

Reference numeral 37 denotes an outer flange portion, and an outer diameter of the outer flange portion 37 is set to be larger than the inner diameter of the shaft holding hole 25, and to be smaller than an inner diameter of the insertion portion conduit-side dimple 27. Reference numeral 38 denotes a circumferential groove for button locking with which an inner flange portion (see reference numeral 11*a* in FIG. 5A) provided on the operation button 11 is engaged.

The first circumferential groove 34*a* is formed closer to the outer flange portion 37. The first seal member 32*a* is in close contact with the bottom surface 27*b* of the insertion portion conduit-side dimple 27. The second circumferential groove 34*b* and the third circumferential groove 34*c* are provided to be separated by a predetermined distance with a dimple communication port 35*a* interposed therebetween.

The second seal member 32b is in close contact with the inner peripheral surface of the shaft holding hole 25.

The gas feeding hole 36 is a hole formed along a shaft center axis a31. The gas feeding hole 36 is set to have a predetermined depth from an end surface of the outer flange portion 37. The gas feeding hole 36 includes an opening formed on the end surface of the outer flange portion 37.

On the other hand, the dimple communication hole 35 includes the dimple communication port 35a and a gas feeding port 35b. The dimple communication port 35a is one opening, and opens to the outer peripheral surface of the shaft 31. The gas feeding port 35b is the other opening, and opens to a bottom side of the inner peripheral surface of the gas feeding hole 36.

The gas feeding/suction valve 10 will be described with reference to FIGS. 5A and 5B.

Figure 5A:
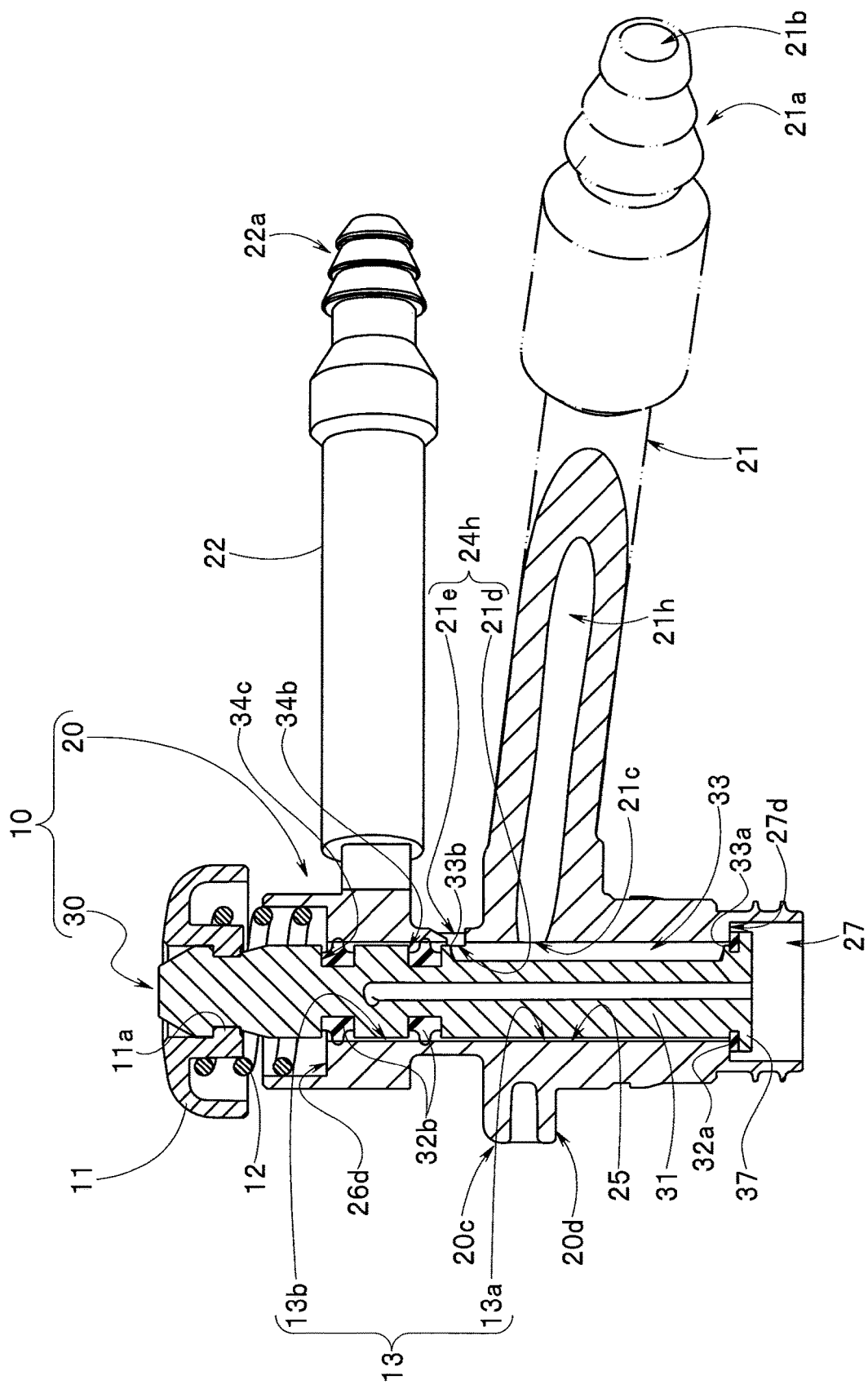
FIG. 5A is a cross-section view taken along a line Y3A-Y3A in FIG. 2B and illustrates a relation of a non-operation state between the cylinder and the piston portion.
Figure 5B:
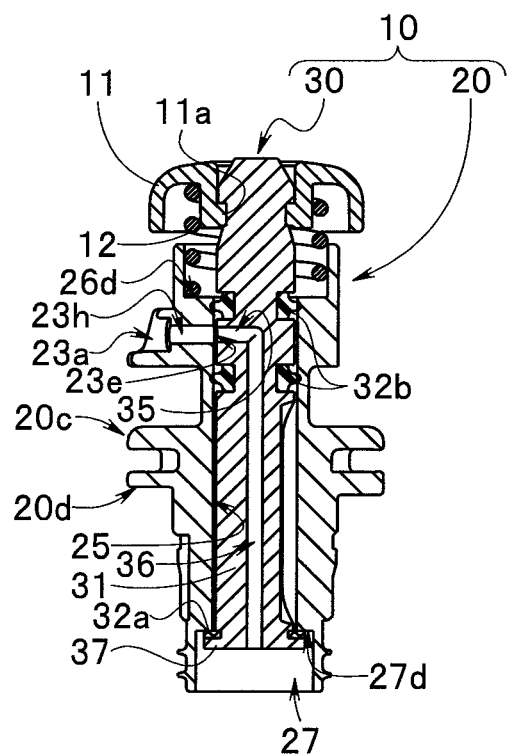
FIG. 5B is a cross-section view taken along the line Y3C-Y3C in FIG. 3B and illustrates a relation of a non-operation state between the cylinder and the piston portion.

As shown in FIGS. 5A and 5B, the gas feeding/suction valve 10 includes the cylinder 20 and the operation member 30 formed integrally. The shaft 31 of the operation member 30 is slidably disposed in the shaft holding hole 25 of the cylinder 20. Therefore, a gap 13 is formed between the outer peripheral surface of the shaft 31 and the inner peripheral surface of the shaft holding hole 25.

The operation button 11 is integrally provided on the shaft 31. The compression coil spring 12 being in a compressed state is disposed between a surface opposite to the operation surface of the operation button 11 and the spring installation surface 26d of the cylinder 20. Therefore, the shaft 31 moves upwards in the drawing by a biasing force of the compression coil spring 12.

Such a moving state is an initial state of the valve and is in a non-operation state. In this state, the first seal member 32a provided on the outer flange portion 37 is in close contact with the flange abutting surface 27d of the insertion portion conduit-side dimple 27. On the other hand, the second seal member 32b provided in the second circumferential groove 34b and the third circumferential groove 34c is in close contact with the inner peripheral surface of the shaft holding hole 25 at a predetermined position.

As a result, the gap 13 includes a first closed space 13a separated by the first seal member 32a and the second seal member 32b of the second circumferential groove 34b and a second closed space 13b separated by the two second seal members 32b. Then, the suction communication dimple 33 is disposed in the first closed space 13a, and the dimple communication port 35a is disposed in the second closed space 13b.

In the initial state of the valve shown in FIG. 5A, the second seal member 32b provided in the second circumferential groove 34b is in close contact with the inner peripheral surface of the shaft holding hole 25 at a position separated from the second side hole 21d toward the operation button 11. The suction communication dimple 33 located in the first closed space 13a communicates with the suction pipe sleeve through-hole 21h of the suction pipe sleeve 21 and also communicates with the suction hole 24h.

Accordingly, in the initial state of the valve, the suction port 21b of the gas feeding/suction valve 10 and the intake port 21e communicating with the outside are brought into communication with each other by the ventilation passage for suction formed by the suction pipe sleeve through-hole 21h, the suction communication dimple 33, and the suction hole 24h.

On the other hand, in the initial state of the valve as shown in FIG. 5B, the gas feeding communication port 23e and the dimple communication port 35a are disposed in the second closed space 13b. For this reason, the inside of the dimple 23a and the inside of the insertion portion conduit-side dimple 27 are brought into communication with each other by the gas feeding through-hole 23h, the dimple communication hole 35, and the gas feeding hole 36.

In other words, when the dimple opening 23m is closed in the initial state of the valve, the gas feeding port 22b of the gas feeding/suction valve 10 and the conduit opening 27m are brought into communication with each other by the fluid path for gas feeding formed by the gas feeding pipe sleeve through-hole 22h, the dimple 23a, the gas feeding through-hole 23h, the dimple communication hole 35, the gas feeding hole 36, and the insertion portion conduit-side dimple 27.

In the initial state of the valve, when the opening 23m shown in FIG. 3B is closed with a finger, the gas feeding pipe sleeve through-hole 22h and the gas feeding through-hole 23h are brought into communication with each other through a space inside the dimple 23a.

The operation of the gas feeding/suction valve 10 will be described below.

Figure 6A:
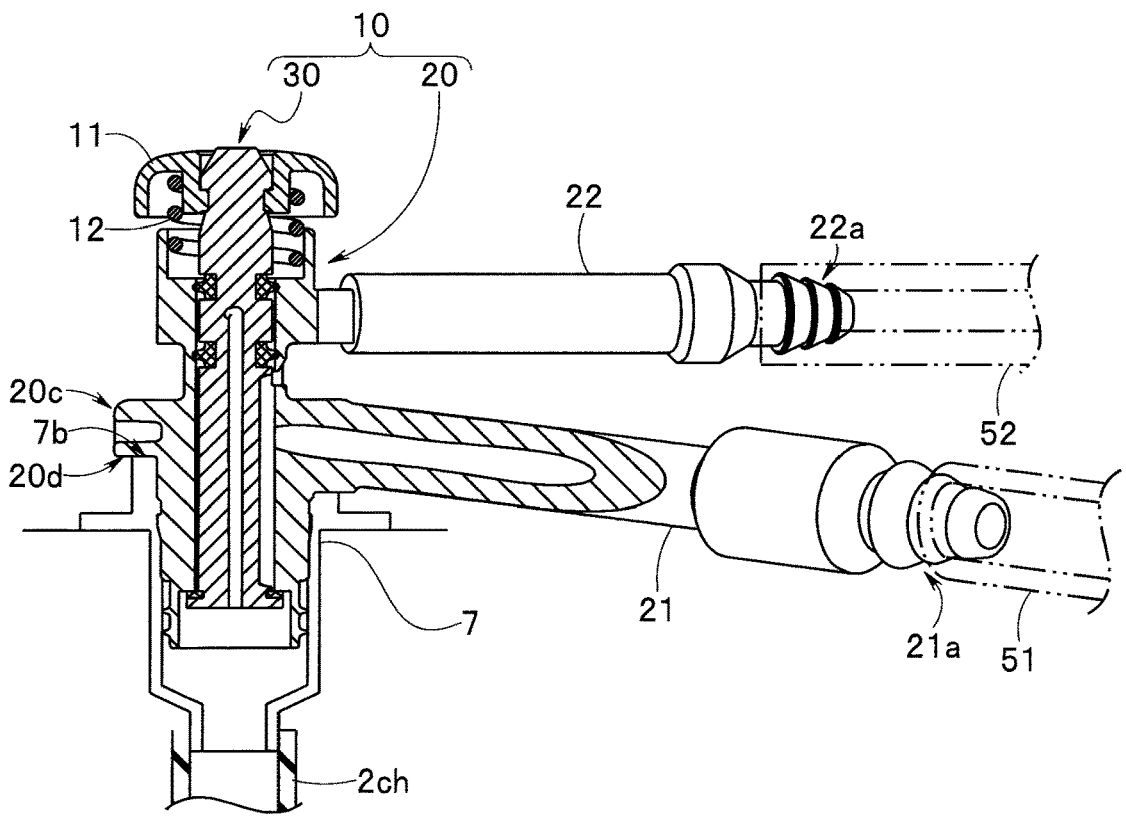
FIG. 6A is a view showing a gas feeding/suction valve attached to the endoscope before observation with the endoscope.

As shown in FIG. 6A, the gas feeding/suction valve 10 is attached to the mounting portion 7. The cylinder abutting surface 20d of the abutting flange 20c of the gas feeding/suction valve 10 abuts on a positioning surface 7b which is an end surface of the mounting portion 7. Reference numeral 2ch is a fluid conduit, one end portion of which is fixed to the mounting portion 7 and the other end portion of which is fixed to a pipe sleeve (not shown) provided on the distal end portion 2a.

The gas feeding/suction valve 10 is attached to an endoscope 1 by a medical professional before an endoscopy. At that time, the medical professional connects the suction tube 51, which extends from suction source (not shown), to the coupling member 21a of the suction tube of the suction pipe sleeve 21 provided in the gas feeding/suction valve 10. Further, the medical professional connects the gas feeding tube 52, which extends from a gas feeding source (not shown), to the coupling member 22a of the gas feeding tube of the gas feeding pipe sleeve 22.

Figure 6B:
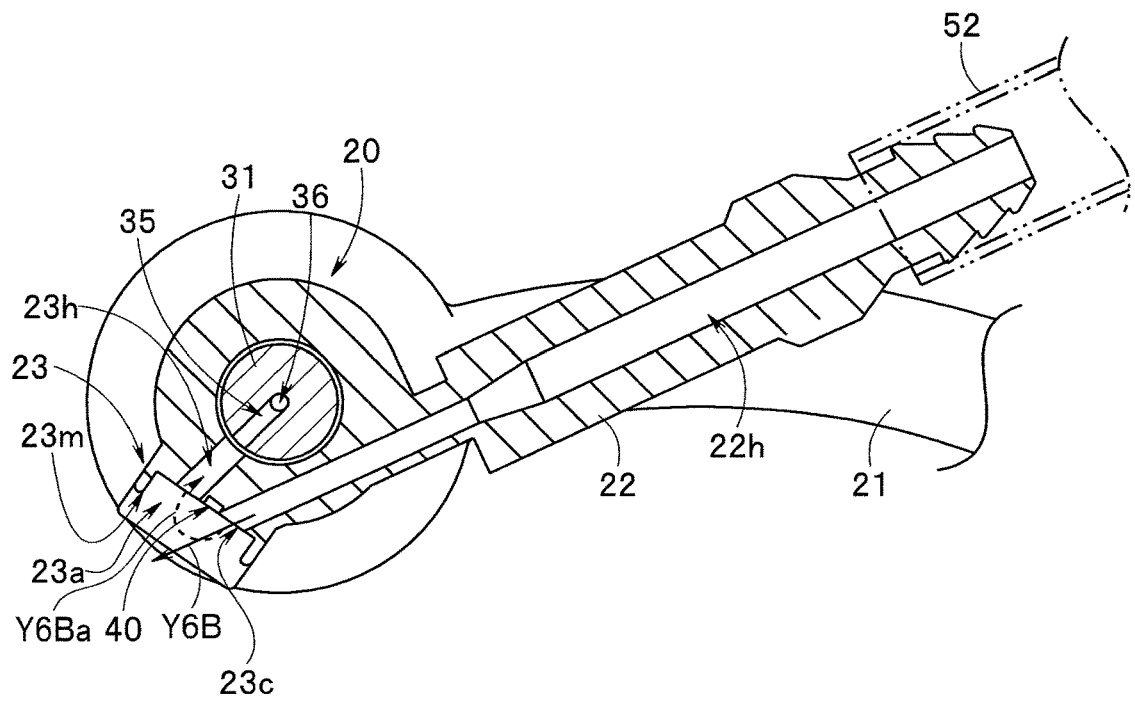
FIG. 6B is a view illustrating a state where gas fed from a gas feeding source jets from an opening and a state where the gas is supplied toward a gas feeding hole.

During a normal connection in which the gas feeding tube 52 is connected to the coupling member 22a of the gas feeding tube, for example, carbon dioxide gas (hereinafter, abbreviated as gas) to be fed from the gas feeding source in a driving state passes through the ventilation passage for gas feeding formed by the gas feeding pipe sleeve through-hole 22h and the dimple 23a as indicated by an arrow Y6B in FIG. 6B and continuously jets to the outside from the dimple opening 23m.

Figure 6C:
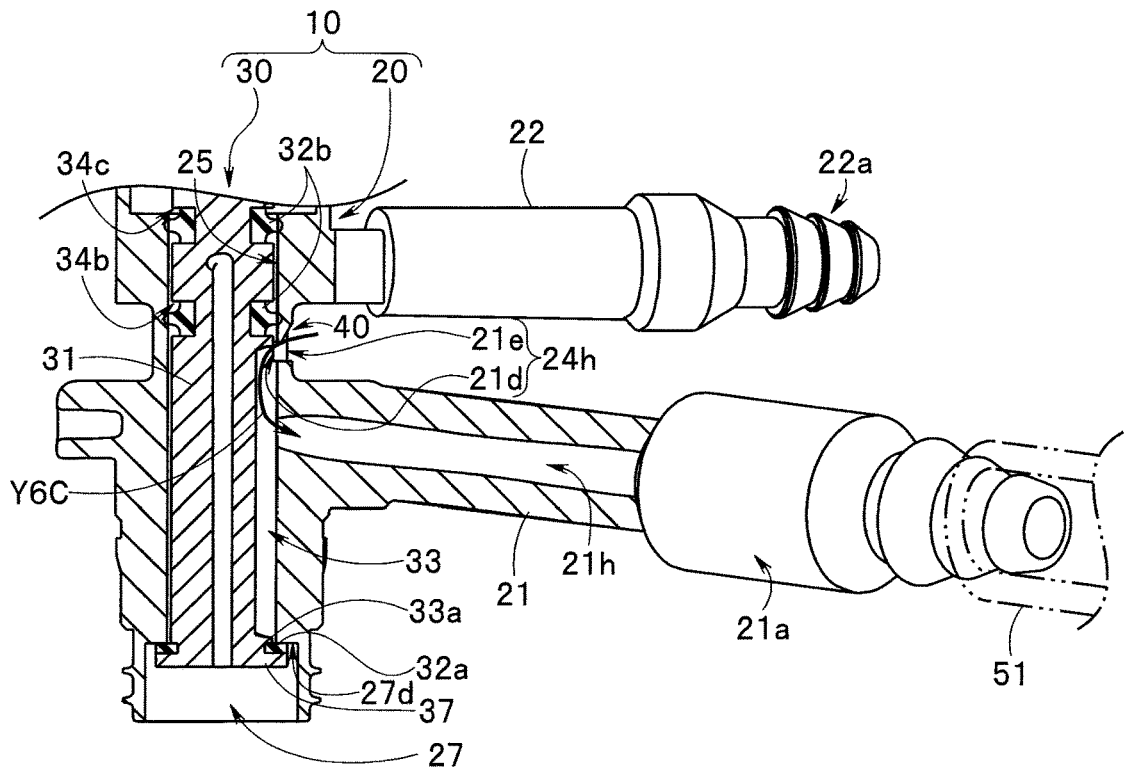
FIG. 6C is a view illustrating a state where a suction tube is normally connected to a suction pipe sleeve.

On the other hand, during a normal connection in which the suction tube 51 is connected to the coupling member 21a of the suction tube, when the intake source is in a driving state, outside air passes through the ventilation passage for intake formed by the suction hole 24h, the suction communication dimple 33, and the suction pipe sleeve through-hole 21h in this order as indicated by an arrow Y6C in FIG. 6C and continues to be sucked by the suction tube 51.

Figure 6D:
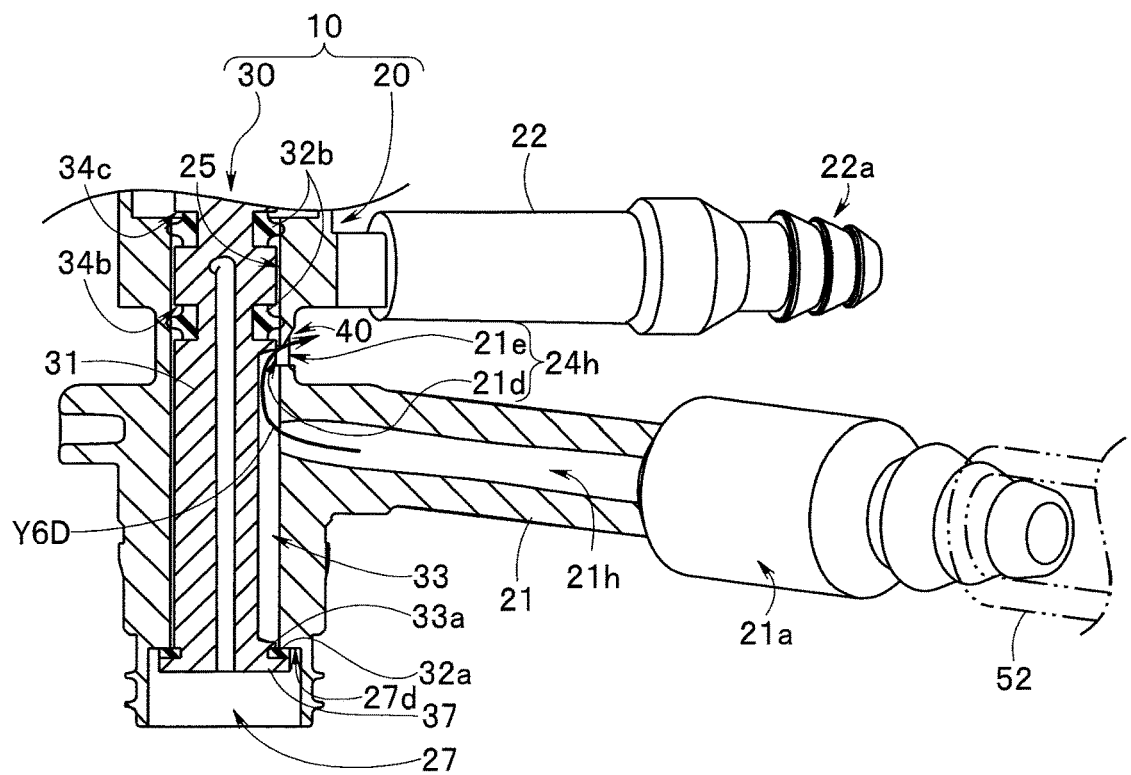
FIG. 6D is a view illustrating a state where a gas feeding tube is erroneously connected to the suction pipe sleeve.

In contrast, during an erroneous connection in which the gas feeding tube 52 is erroneously connected to the coupling member 21a of the suction tube as shown in FIG. 6D, the gas to be fed from the gas feeding source flows in the ventilation passage for intake in a direction opposite to the flowing direction of the air during the normal connection.

In other words, the gas flows in the suction pipe sleeve through-hole 21h, the suction communication dimple 33, and the suction hole 24h in this order as indicated by an arrow Y6D and jets to the outside from the intake port 21e.

The sounding body 40 is provided near the intake port 21e. At the time of erroneous connection, the gas is flowing in the suction hole 24h in the opposite direction. Due to the gas flowing in the direction opposite to the direction in which the gas to be fed from the gas feeding source is supposed to flow, the sounding body 40 makes a warning sound that gives an unpleasant feeling.

The medical professional can confirm the warning sound to recognize the state where the gas feeding tube 52 is erroneously connected to the suction pipe sleeve 21. After recognizing the state, the medical professional removes the erroneously connected gas feeding tube 52 from the coupling member 21a of the suction tube, and reconnects the gas feeding tube to the coupling member 22a of the gas feeding tube of the gas feeding pipe sleeve 22.

Thus, the connection of the gas feeding tube 52 to the coupling member 22a of the gas feeding tube is completed.

Figure 6E:
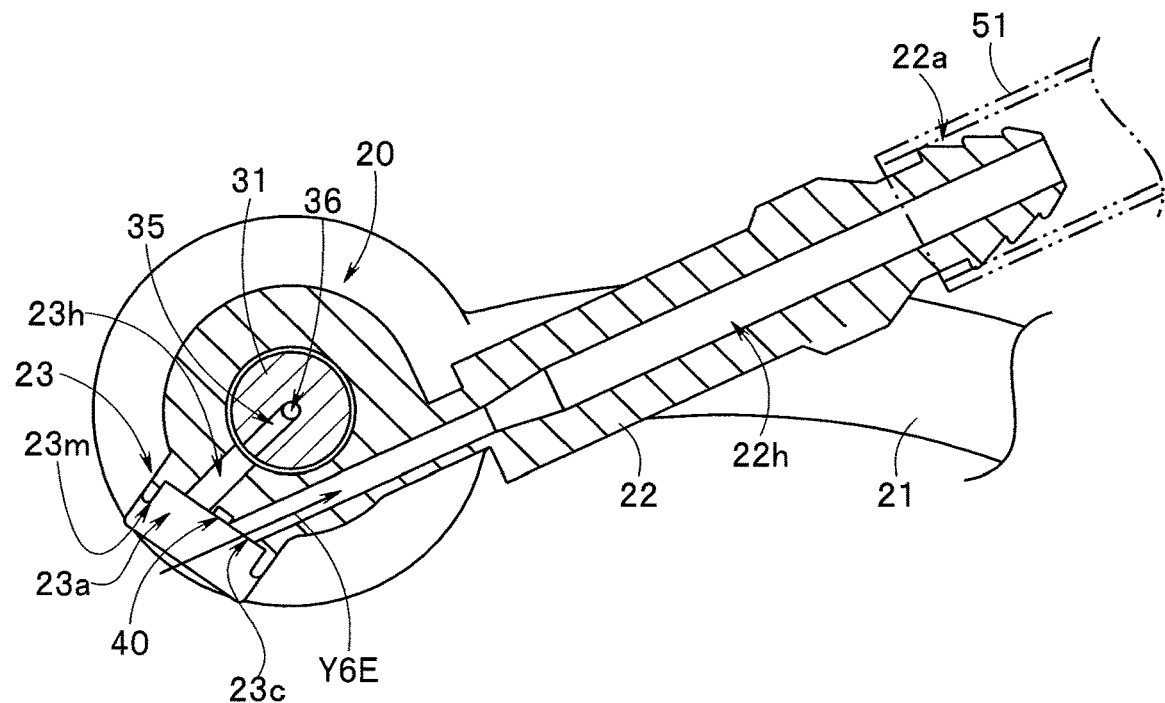
FIG. 6E is a view illustrating a state where the suction tube is erroneously connected to the gas feeding pipe sleeve.

On the other hand, during an erroneous connection in which the suction tube 51 is erroneously connected to the coupling member 22a of the gas feeding tube as shown in FIG. 6E, the outside air flows in a direction of an arrow Y6E due to an intake action of the suction source. In other words, the air flows in the dimple 23a and the gas feeding pipe sleeve through-hole 22h in this order and is continuously sucked by the suction tube 51.

Figure 7A:
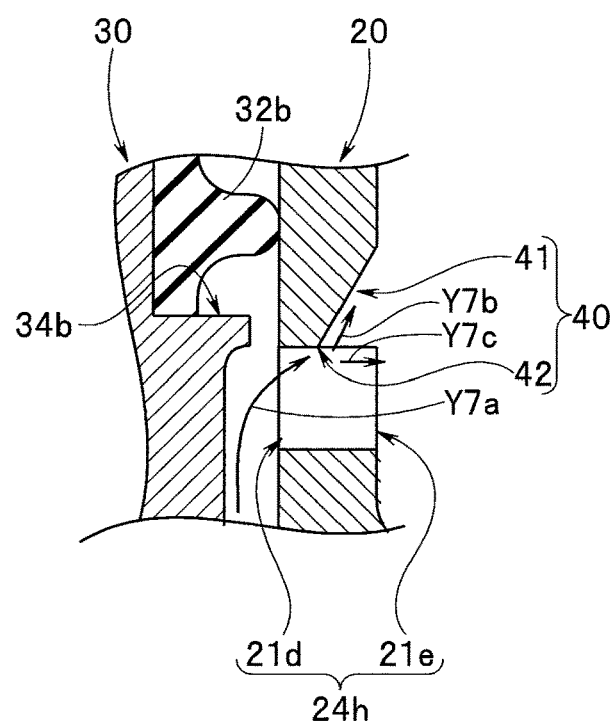
FIG. 7A is a view illustrating a first sounding body provided in a suction hole.
Figure 7B:
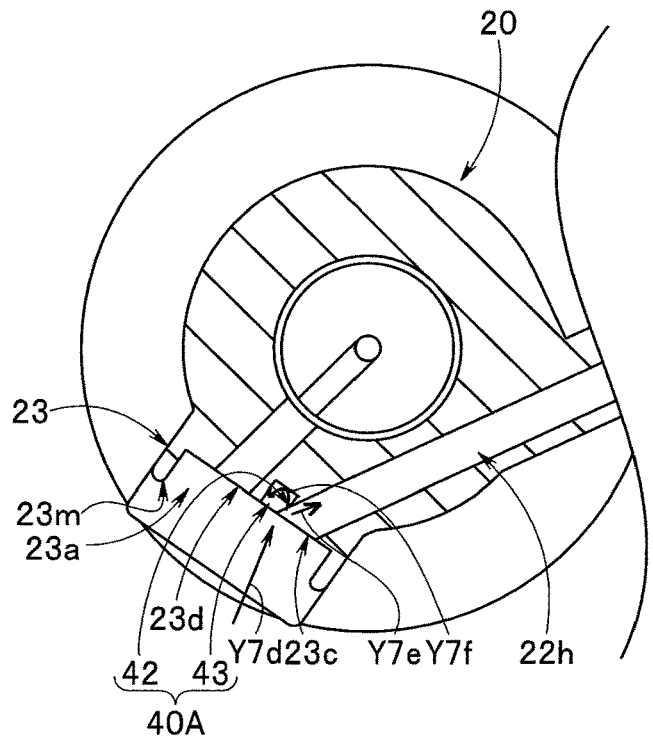
FIG. 7B is a view illustrating a second sounding body provided in a dimple.

As shown in FIG. 7B, a second sounding body 40A is provided near the first dimple opening 23c. Hereinafter, the second sounding body 40A may be referred to as a sounding body 40A. At the time of erroneous connection, the air flows in the opposite direction from the first dimple opening 23c. Due to the air flowing in the direction opposite to the direction in which the gas to be taken in from the suction source is supposed to flow, the sounding body 40A makes a warning sound that gives an unpleasant feeling.

The medical professional can confirm the warning sound to recognize the state where the suction tube 51 is erroneously connected to the gas feeding pipe sleeve 22. After recognizing the state, the medical professional removes the erroneously connected suction tube 51 from the coupling member 22a of the gas feeding tube, and reconnects the suction tube to the coupling member 21a of the suction tube of the suction pipe sleeve 21.

Thus, the connection of the suction tube 51 to the coupling member 21a of the suction tube is completed.

The sounding body 40 or 40A will be described with reference to FIG. 7A or 7B.

The sounding body has a structure similar to a mouthpiece of a recorder, and is configured such that air flows toward an edge and a sound is produced when the air hits the edge and changes into two flows.

As shown in FIG. 7A, the sounding body 40 provided in the suction hole 24h is an edge 42 formed by providing a notch 41 on the side of the intake port 21e of the suction hole 24h.

In the sounding body 40, the gas fed from the gas feeding source flows from the second side hole 21d toward the intake port 21e as indicated by an arrow Y7a, so that the gas changes to two flows in the vicinity of the edge 42 as indicated by arrows Y7b and Y7c and makes a warning sound.

As shown in FIG. 7B, the second sounding body 40A provided in the dimple 23a is an edge 42 formed by providing a dimple 43 between the first dimple opening 23c and the second dimple opening 23d.

In the second sounding body 40A, the air to be sucked flows from the dimple opening 23m to the first dimple opening 23c as indicated by an arrow Y7d, so that the air hits the edge 42 and changes to a flow proceeding into the gas feeding pipe sleeve through-hole 22h as indicated by an arrow Y7e and a flow proceeding into the dimple 43 as indicated by an arrow Y7f to make a warning sound.

In the normal connection in which the air flows in the direction opposite to the arrow, no warning sound is generated. In addition, a tone of the warning sound is determined by adjustment of shapes and sizes of the notch 41 and the dimple 43. Further, for the purpose of adjusting the direction of the air hitting the edge 42, an adjustment portion configured to change the flow of gas may be provided on the bottom surface of the suction communication dimple 33 and the inner surface of the dimple 43 to adjust the tone of the warning sound.

As described above, the cylinder body 20b is provided with the suction hole 24h configured to suck the outside air when the suction source is in an operation state and the dimple 23a including the dimple opening 23m through which the air jets to the outside when the gas feeding source is in an operation state. Then, the sounding body 40 or 40A is provided near the intake port 21e of the suction hole 24h, and the sounding body 40A is provided near the first dimple opening 23c in the dimple 23a.

Thus, during the gas feeding state in which the gas feeding tube 52 extending from the gas feeding source is erroneously connected to the suction pipe sleeve 21 and during the suction state in which the suction tube 51 extending from the suction source is erroneously connected to the gas feeding pipe sleeve 22, since the air flows into the intake port 21e and the first dimple opening 23c in the direction opposite to the direction in the normal connection, the sounding body 40 or 40A makes the warning sound, and the erroneous connection of the tube can be instantly determined.

Since the gas feeding source is driven in advance when the gas feeding tube 52 is connected to the coupling member 21a of the suction tube of the suction pipe sleeve 21, the warning sound is generated in the state where the end portion of gas feeding tube 52 is disposed on the coupling member 21a of the suction tube, and the erroneous connection can be determined before the completion of the connection.

Similarly, even when the suction tube 51 is disposed on the coupling member 22a of the gas feeding tube of the gas feeding pipe sleeve 22 in the state where the intake source is driven, the erroneous connection can be determined before the completion of the connection. As a result, the erroneous connection of the tube to the pipe sleeve is eliminated.

In addition, since the sounding body 40 is provided, the valve body portion configured to avoid the gas feeding through the suction path becomes unnecessary. For this reason, the number of components can be reduced, the assembling work of the valve body portion becomes unnecessary, and thus an inexpensive fluid control device for endoscope can be realized.

Confirmation of the gas feeding and confirmation of the suction will be described below.

The medical professional performs the work to confirm whether the gas is fed from the conduit opening 27m or is sucked from the conduit opening 27m after the completion of the normal connection in which the suction tube 51 and the gas feeding tube 52 are connected to the suction pipe sleeve 21 and the gas feeding pipe sleeve 22, respectively.

First, the confirmation work of the gas feeding will be described.

The medical professional closes the dimple opening 23m with a finger. Then, a finger pulp is pushed by a jetting pressure of the gas to be fed from the gas feeding source. Here, the medical professional continues to close the dimple opening 23m against the jetting pressure. As a result, the gas flows into the gas feeding through-hole 23h as indicated by a dashed arrow Y6Ba in FIG. 6B. Thereafter, the gas passes through the dimple communication hole 35, the gas feeding hole 36, the insertion portion conduit-side dimple 27 shown in FIG. 5B and jets from the conduit opening 27m.

Thus, the medical professional determines that the gas feeding function is working normally. On the other hand, when a jetting force of the gas jetting from the conduit opening 27m is weak, or when the jetting cannot be confirmed, the medical professional determines to be a defective product. In this case, the medical professional prepares another gas feeding/suction valve 10 and performs reconnection of the tubes 51 and 52.

Next, the confirmation work of the suction will be described below.

Figure 8A:
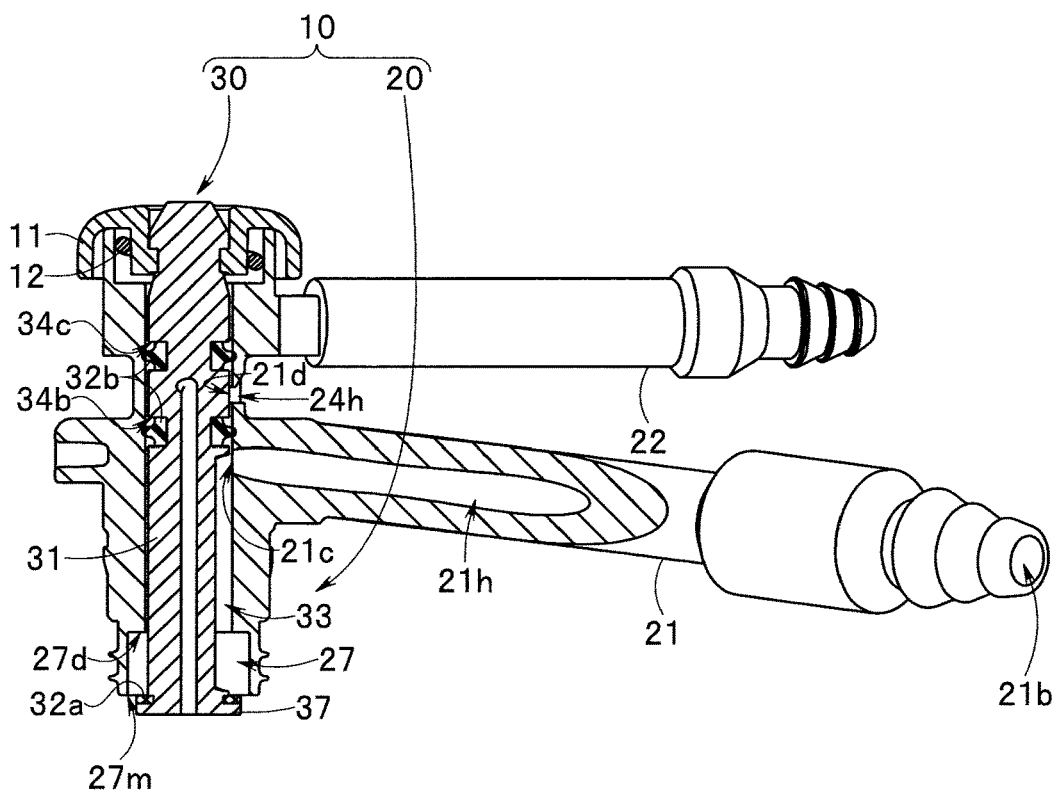
FIG. 8A is a view illustrating a relation between the suction hole and the suction pipe sleeve through-hole during a suction operation and a fluid path for suction formed by the suction pipe sleeve through-hole, a suction communication dimple, and an insertion portion conduit-side dimple.
Figure 8B:
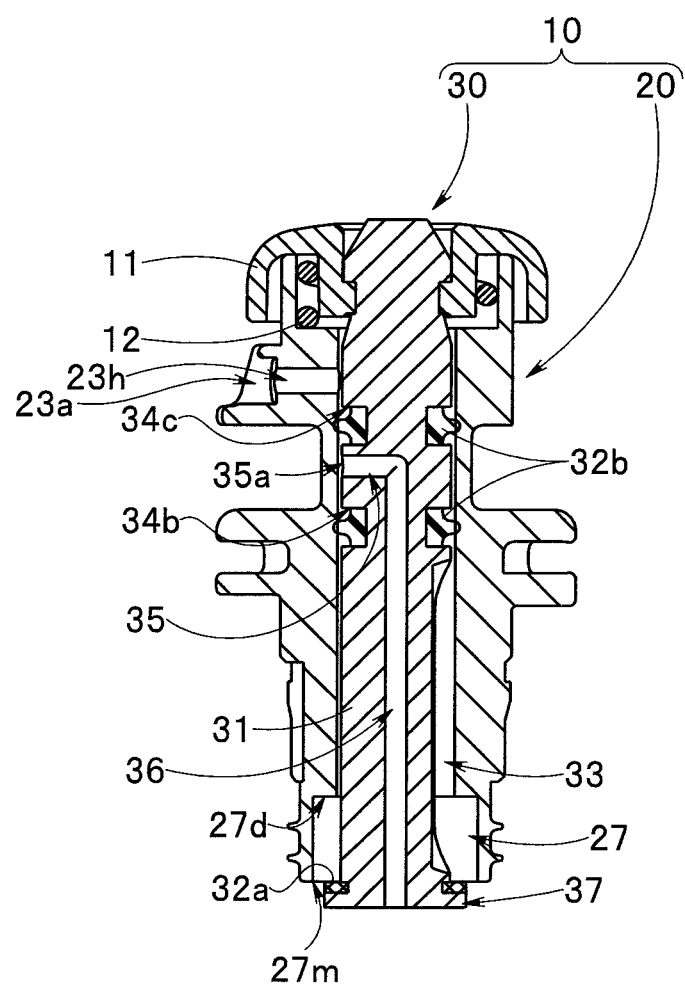
FIG. 8B is a view illustrating a relation between a gas feeding through-hole and a dimple communication hole during the suction operation.

The medical professional pushes down the operation button 11 located in the initial state of the valve with a finger against the biasing force of the compression coil spring 12 to switch the operation button to the suction operation state shown in FIGS. 8A and 8B.

Then, the outer flange portion 37 moves to be disposed outwards from the conduit opening 27m of the insertion portion conduit-side dimple 27. As a result, the insertion portion conduit-side dimple 27 and the suction communication dimple 33 are brought into communication with each other. Further, the second seal member 32b provided in the second circumferential groove 34b is disposed between the second side hole 21d and the first side hole 21c. As a result, the communication state between the suction hole 24h and the suction pipe sleeve through-hole 21h is released.

In addition, the second seal member 32b provided in the third circumferential groove 34c moves downwards from the gas feeding communication port 23e in the drawing. As a result, the communication state between the gas feeding through-hole 23h and the dimple communication hole 35 is released.

Therefore, the suction port 21b and the conduit opening 27m of the gas feeding/suction valve 10 are brought into communication with each other through the fluid path for suction formed by the suction pipe sleeve through-hole 21h, the suction communication dimple 33, and the insertion portion conduit-side dimple 27, and the suction state can be obtained.

Thus, the medical professional determines that the suction function is working normally. On the other hand, when the amount of suction through the conduit opening 27m is weak, or when the suction cannot be confirmed, the medical professional determines to be a defective product. In this case, the medical professional prepares another gas feeding/suction valve 10 and performs reconnection of the tubes 51 and 52 as described above.

The medical professional attaches the gas feeding/suction valve 10, which is determined that the gas feeding function and the suction function are normal, to the mounting portion 7 of the operation portion 3 as described above.

In the embodiment described above, the sounding body 40 is provided near the intake port 21e of the suction hole 24h, and the sounding body 40A is provided near the first dimple opening 23c in the dimple 23a. However, the sounding body 40 may be provided near the intake port 21e of the suction hole 24h, or the sounding body 40A may be provided near the first dimple opening 23c in the dimple 23a. In other words, the gas feeding/suction valve of the embodiment may have at least one sounding body.

In a case where the second sounding body 40A is provided and the first sounding body 40 is not provided, when the suction tube 51 is erroneously connected to the gas feeding pipe sleeve 22, the sounding body 40A can make a warning sound to confirm the erroneous connection as described above.

When the gas feeding tube 52 is erroneously connected to the suction pipe sleeve 21, the air jets from the intake port 21e instead of the generation of the warning sound. Therefore, the medical professional can recognize the erroneous connection by bringing the finger close to the intake port 21e and confirming the jetting.

On the other hand, in a case were the first sounding body 40 is provided and the second sounding body 40A is not provided, when the gas feeding tube 52 is erroneously connected to the suction pipe sleeve 21, the sounding body 40 can make a warning sound to confirm the erroneous connection as described above.

When the suction tube 51 is erroneously connected to the gas feeding pipe sleeve 22, the air is taken into the gas feeding pipe sleeve through-hole 22h from the first dimple opening 23c instead of the generation of the warning sound. The medical professional closes the dimple opening 23m with a finger in order to feed the gas. Thus, the finger pulp is sucked into the dimple 23a due to the suction force of the intake source, and thus the erroneous connection can be recognized.

As described above, even when the sounding body is provided near only one of the intake port 21e of the suction hole 24h and the first dimple opening 23c of the dimple 23a, the erroneous connection can be prevented.

In the embodiment described above, the gas feeding/suction valve 10 is used as the fluid control device for endoscope. However, a dedicated suction valve may be used as the fluid control device for endoscope.

In the suction valve, the gas feeding pipe sleeve 22 and the leak projection 23 including the gas feeding pipe sleeve through-hole 22h protruding from the outer peripheral surface of the cylinder 20, the dimple communication hole 35 of the shaft 31 of the operation member 30, the gas feeding hole 36, and the circumferential grooves 34b and 34c are unnecessary. Other components are similar to the components of the embodiment described above.

In the suction valve, during the erroneous connection in which the gas feeding tube 52 is erroneously connected to the suction pipe sleeve 21, a warning sound is generated from the sounding body 40. Therefore, in the normal suction operation state, as described above, the insertion portion conduit-side dimple 27 and the suction communication dimple 33 are brought into communication with each other, and the suction state can be obtained.

According to the present invention, it is possible to realize the fluid control device for endoscope that solves the problem that the pipe sleeve having a predetermined function is erroneously connected with the fluid tube having a function different from the predetermined function.

The present invention is not limited to the embodiment described above, and various modifications can be made without departing from the gist of the invention.

What is claimed is:

1. A fluid control device for use with an endoscope, the fluid control device comprising:
   a cylinder that is attachable to an operation portion of an endoscope and includes a conduit opening communicable with a fluid conduit provided inside an insertion portion of the endoscope;

two coupling members provided at different positions from the conduit opening of the cylinder and connected to respective fluid sources configured to execute predetermined functions; and an operation member provided inside the cylinder and including a shaft slidably disposed in a space forming respective fluid paths through which openings of the two coupling members and the conduit opening communicate with each other, wherein the cylinder includes a sounding body provided near at least one of two ventilation ports, through which the fluid paths communicate with an outside of the cylinder, the sounding body being configured to generate a sound when a fluid flows in a second direction opposite to a first direction in which a fluid generated from one of the fluid sources is supposed to flow, and configured not to generate the sound when the fluid flows in the first direction;

wherein the sounding body comprises a surface configured to separate the fluid flow in the second direction into two separate fluid flows to generate the sound and to not separate the fluid flow in the first direction to not generate the sound.

2. The fluid control device according to claim 1, wherein each of the fluid paths is a fluid path for suction, and the sounding body is a first sounding body provided near a suction port of the at least two ventilation ports, and the sounding body is configured to generate a sound when the gas feeding source, which is one of the fluid sources, is connected to a suction pipe sleeve including any of the two coupling members and a gas feeding fluid jets from any of the two coupling members.

3. The fluid control device according to claim 2, wherein the shaft is provided with a plurality of seal members configured to bring the suction port and the suction pipe sleeve into communication with each other in a non-operation state and to block the communication between the suction port and the suction pipe sleeve in an operation state.

4. The fluid control device according to claim 3, wherein on an outer peripheral surface of the shaft, a communication path serving as a part of a fluid path for suction is formed to bring the suction pipe sleeve and the conduit opening into communication with each other in the operation state.

5. The fluid control device according to claim 4, wherein the cylinder is formed with:

a dimple including a jet port, through which a gas feeding fluid to be supplied from the gas feeding source connected to a gas feeding pipe sleeve to a fluid path for gas feeding jets to an outside of the cylinder, as the ventilation port on an inner surface, the gas feeding source being connected to the gas feeding pipe sleeve; and an inlet port provided adjacent to the jet port on the inner surface of the dimple and serving as an opening of a fluid path communicating with the space, wherein the cylinder further includes a second sounding body provided near the jet port and configured to generate a sound when the suction source is connected to the gas feeding pipe sleeve and air flows in from the jet port, and the shaft includes a communication path serving as a part of a fluid path for gas feeding through which an inside of the dimple and the conduit opening communicate with each other in the non-operation state.

6. The fluid control device according to claim 5, wherein the shaft includes three circumferential grooves in which the seal members are disposed, respectively, and a seal member disposed in a first circumferential groove of the three circumferential grooves in the non-operation state blocks communication between the conduit opening and the communication path serving as the part of the fluid path for suction.

7. The fluid control device according to claim 6, wherein a seal member disposed in a second circumferential groove of the three circumferential grooves in the non-operation state and a seal member disposed in a third circumferential groove of the three circumferential grooves are disposed to sandwich a gas feeding communication port, which is an opening at another end of the inlet port, and bring the inside of the dimple and the conduit opening into communication with each other.

8. The fluid control device according to claim 7, wherein the seal member disposed in the third circumferential groove in the operation state moves to a position where the inside of the dimple and the conduit opening are not brought into communication with each other.

9. The fluid control device according to claim 7, wherein the seal member disposed in the second circumferential groove in the operation state moves to a position where communication between the suction port and the suction pipe sleeve is blocked.

10. The fluid control device according to claim 5, wherein the dimple includes a dimple opening that opens to an outer peripheral surface side of the cylinder, and in a jetting state in which a fluid fed from the gas feeding source jets from the jet port, the dimple opening is closed, so that the fluid fed from the gas feeding source flows from the inlet port to a gas feeding through-hole communicating with the space.

11. An endoscope comprising:

an insertion portion including a fluid conduit therein;

an operation portion provided continuously to the insertion portion; and a fluid control device for endoscope, the fluid control device for endoscope including:

a cylinder that is attachable to the operation portion and includes a conduit opening communicable with a fluid conduit provided inside the insertion portion;

two coupling members provided at different positions from the conduit opening of the cylinder and connected to respective fluid sources configured to execute predetermined functions; and an operation member provided inside the cylinder and including a shaft slidably disposed in a space forming respective fluid paths through which openings of the two coupling members and the conduit opening communicate with each other, the cylinder including a sounding body provided near at least one of two ventilation ports, through which the fluid paths communicate with an outside of the cylinder, the sounding body being configured to generate a sound when a fluid flows in a second direction opposite to a first direction in which a fluid generated from one of the fluid sources is supposed to flow, and configured not to generate the sound when the fluid flows in the first direction;

wherein the sounding body comprises a surface configured to separate the fluid flow in the second direction into two separate fluid flows to generate the sound and to not separate the fluid flow in the first direction to not generate the sound.

12. A fluid control device for use with an endoscope, the fluid control device comprising:

a cylinder that is attachable to an operation portion of an endoscope and includes a conduit having a conduit opening communicable with a fluid conduit provided inside an insertion portion of the endoscope, the cylinder having:
  a first coupling member having a first fluid channel in communication with the conduit; and
  a second coupling member having a second fluid channel in communication with the conduit; and
an operation member provided inside the cylinder and including a shaft slidably disposed in a space forming first and second fluid paths through the first and second coupling members, respectively; wherein
wherein the cylinder includes at least one sounding body being configured to at least one of:
  generate a sound when a first fluid flows into the conduit from the first coupling member and configured not to generate the sound when the first fluid flows out from the conduit through the first coupling member; and
  generate a sound when a second fluid flows out from the conduit from the second coupling member and configured not to generate the sound when the first fluid flows into the conduit through the second coupling member.

13. The fluid control device according to claim 12, wherein the at least one sounding body comprises a surface configured to at least one of:

separate the first fluid flow into the conduit to generate the sound and to not separate the first fluid flow out from the conduit to not generate the sound; and separate the second fluid flow out from the conduit to generate the sound and to not separate the second fluid flow into the conduit to not generate the sound.

14. The fluid control device according to claim 12, wherein the at least one sounding body comprises:
a first sounding body configured to generate the sound when the first fluid flows into the conduit from the first coupling member and configured not to generate the sound when the first fluid flows out from the conduit through the first coupling member; and
a second sounding body configured to generate the sound when a second fluid flows out from the conduit from the second coupling member and configured not to generate the sound when the first fluid flows into the conduit through the second coupling member.

15. An endoscope comprising:
an insertion portion including a fluid conduit therein;
an operation portion provided continuously to the insertion portion; and
the fluid control device according to claim 12,
wherein the cylinder is attached to the operation portion such that the conduit is in fluid communication with the fluid conduit provided inside the insertion portion.

* * * * *